United States Patent [19]

Kobayashi et al.

[11] Patent Number: 4,593,701

[45] Date of Patent: Jun. 10, 1986

[54] CATHETER-TIP MICROMANOMETER UTILIZING SINGLE POLARIZATION OPTICAL FIBER

[75] Inventors: Kenji Kobayashi, Yokohama; Tsutomu Yasuda, Kawasaki; Hiroshi Matsumoto, Higashi Kanamachi; Humiki Sone, Hitachi, all of Japan

[73] Assignee: Hitachi Cable, Ltd., Tokyo, Japan

[21] Appl. No.: 643,291

[22] Filed: Aug. 22, 1984

[30] Foreign Application Priority Data

Apr. 16, 1984 [JP] Japan .................. 59-77100

[51] Int. Cl.⁴ .................. A61B 5/02; A61B 5/00
[52] U.S. Cl. .................. 128/667; 128/634; 128/673; 73/705
[58] Field of Search .................. 128/672–673, 128/675, 748, 634, 667; 73/705, 708, 715

[56] References Cited

U.S. PATENT DOCUMENTS

| | | | |
|---|---|---|---|
| 3,215,135 | 11/1965 | Franke | 128/675 |
| 3,249,105 | 5/1966 | Polanyi | 128/675 |
| 3,267,932 | 8/1966 | Valliere | 128/675 |
| 3,498,286 | 3/1970 | Polanyi et al. | 128/673 X |
| 3,686,958 | 8/1972 | Porter et al. | 128/748 X |
| 3,789,667 | 2/1974 | Porter et al. | 128/748 X |
| 4,201,222 | 5/1980 | Haase | 128/667 X |
| 4,210,029 | 7/1980 | Porter | 128/673 X |
| 4,487,206 | 12/1984 | Aagard | 128/673 X |

*Primary Examiner*—Kyle L. Howell
*Assistant Examiner*—Angela D. Sykes
*Attorney, Agent, or Firm*—Antonelli, Terry & Wands

[57] ABSTRACT

A catheter-tip micromanometer includes a photoelastic element, with the photoelastic element changing light propagation constants of two axes perpendicular to each other in response to blood pressure level and direction to which blood pressure is applied. Light is propagated through the photoelastic element at a prescribed angle with regard to the two axes thereof perpendicular to each other by means of a single polarization optical fiber which maintains a plane of polarization whereby blood pressure is measured on the basis of a difference between propagation velocities in two axial directions obtained during the propagation.

11 Claims, 18 Drawing Figures

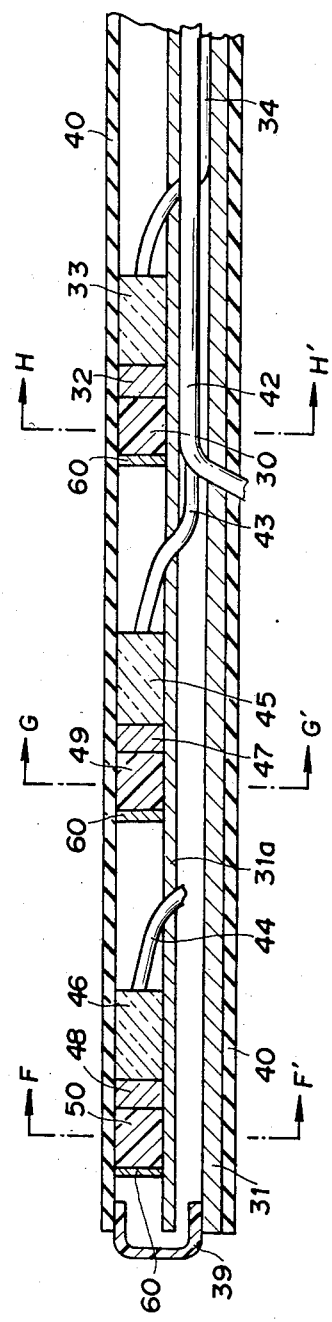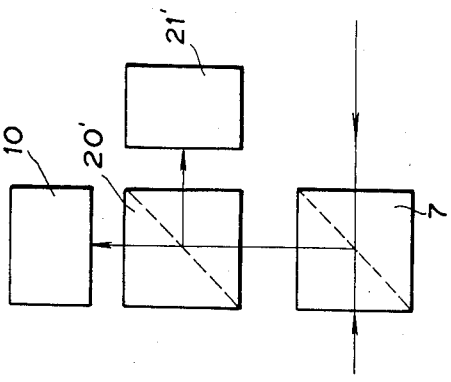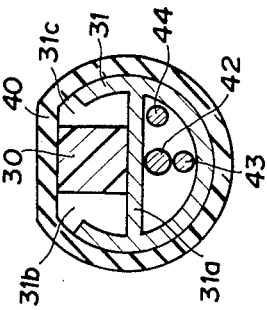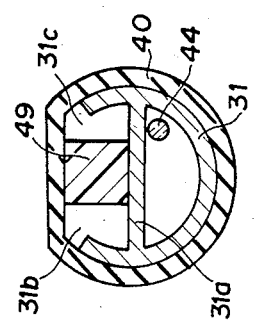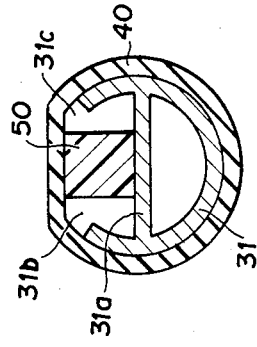

CATHETER-TIP MICROMANOMETER UTILIZING SINGLE POLARIZATION OPTICAL FIBER

BACKGROUND OF THE INVENTION

This invention relates to a catheter-tip micromanometer utilizing a single polarization optical fiber, and more particularly, to a catheter-tip micromanometer utilizing a single polarization fiber which can be miniaturized and reduced in diameter, besides which can easily fabricated while maintaining high performance of the micromanometer.

DESCRIPTION OF THE PRIOR ART

A catheter-tip micromanometer utilizing optical fibers is safer than that of electrical type, when applied to human bodies, so that the micromanometer utilizing optical fibers exhibits excellent applicability as a clinical instrument. The construction of such micromanometer utilizing optical fibers is as shown in FIG. 1a wherein a diaphragm 2, supported by a fixture 3, is combined with an optical fiber bundle generally designated by the reference numeral 1, a light source 4, and a receptor 5, respectively. The optical fiber bundle 1 consists of a light-supplying fiber group 1a which transmits light from the light source 4, and a light-receiving fiber group 1b which transmits light to the receptor 5, and with the groups 1a, 1b being combined at point B. In order to elevate sensitivity of the end surface 1c of the combined light-supplying and light-receiving fiber groups 1a, 1b, light-supplying fiber core wires a are disposed intimately adjacent to light-receiving fiber core wires b each other as shown in FIG. 1b. A diameter of the diaphragm fixture 3 may be made within a range of about 1 mm–2 mm in order that blood pressure can be measured in a narrow space of a human body.

In operation of the above construction of the catheter-tip micromanometer utilizing optical fibers, light emitted from the light source 4 reaches the diaphragm 2 through the light-supplying fiber 1a, and the light reflected by the diaphragm 2 reaches the receptor 5 through the light-receiving fiber group 1b. When a pressure P is applied to the diaphragm 2, it is deformed in response to the pressure P and a distance between the diaphragm 2 and an end surface 1c of the fiber bundle 1 changes, so that coupling efficiency from the light-supplying fiber group 1a to the light-receiving fiber group 1b varies and light level received by the receptor 5 also changes. A value of blood pressure is measured by such a change in light level.

However, if the diaphragm 2, having a small area, is used, amount of deformation also becomes small with respect to the identical pressure and, as a result, change in light-receiving level is also slight in the receptor 5 so that there is such a fear that value of blood pressure is not correctly measured. In order to elevate sensitivity, even in a small diameter diaphragm 2, it is necessary to increase number of optical fiber core wires of the optical fiber bundle 1. Thus, there is a limitation for reducing diameter in such an instrument. For improving sensitivity in such instrument, the light-supplying fiber core wires a must be disposed in such that they are intimately adjacent to the light-receiving fiber core wires b in the end surface 1c of the optical fiber bundle 1 facing the diaphragm 2. A disadvantage of this approach resides in the fact that it becomes difficult to arrange the optical fiber bundle 1 and to fabricate the catheter-tip micromanometer utilizing optical fibers as mentioned above.

SUMMARY OF THE INVENTION

It is an object of the present invention to provide a catheter-tip micromanometer utilizing a single polarization optical fiber which can be miniaturized and reduced in diameter while maintaining high performance of the micromanometer, and which can easily be fabricated.

Another object of the present invention resides in providing a catheter-tip micromanometer utilizing a single polarization optical fiber wherein external pressure is applied only unidirectionally to a photoelastic element.

Yet another object of the present invention resides in providing a catheter-tip micromanometer utilizing a single polarization optical fiber by which changes in positive and negative directions can be measured without decreasing sensitivity even in case of $p \simeq 0$ ($\alpha << 1$), in a manner described more fully herein below.

A further object of the invention resides in providing a catheter-top micromanometer utilizing a single polarization optical fiber which cannot adversely be affected by reflected light and the like with respect to a light source.

A still further object of the invention resides in providing a catheter-tip micromanometer utilizing a single polarization optical fiber which can collect blood in addition to measurement of blood pressure.

Yet another object of the invention resides in providing a catheter-tip micromanometer utilizing a single polarization optical fiber which can detect blood pressure at plural positions along the longitudinal direction thereof.

BRIEF DESCRIPTION OF THE DRAWINGS

FIG. 1b is a sectional view taken along line A—A' of FIG. 1a;

FIG. 6b is a sectional view taken along line B—B' of FIG. 6a;

FIG. 7b is a sectional view taken along line C—C' of FIG. 7a;

FIG. 8b is a sectional view taken along line D—D' of FIG. 8a;

FIG. 9a is a cross-sectional view of a principal part of the catheter-tip micromanometer utilizing a single polarization fiber in accordance with yet another embodiment of the present invention;

FIGS. 9b to 9d are sectional views taken along lines F—F', G—G' and H—H' of FIG. 9a; and FIG. 10 is a schematic view of another embodiment of light-receiving part in the catheter-tip micromanometer utilizing a single polarization fiber according to the present invention.

DETAILED DESCRIPTION OF THE INVENTION

Figure 1A:
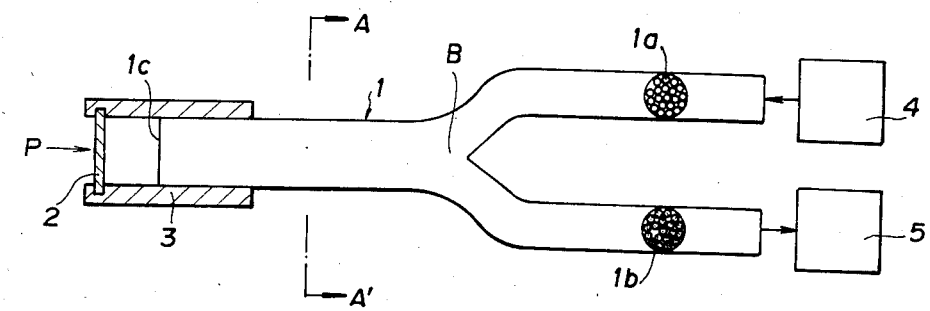
FIG. 1a is partially schematic cross-sectional view of a construction of a conventional catheter-tip micromanometer.
Figure 1B:
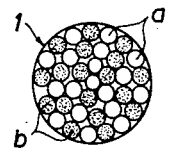
Figure 2:
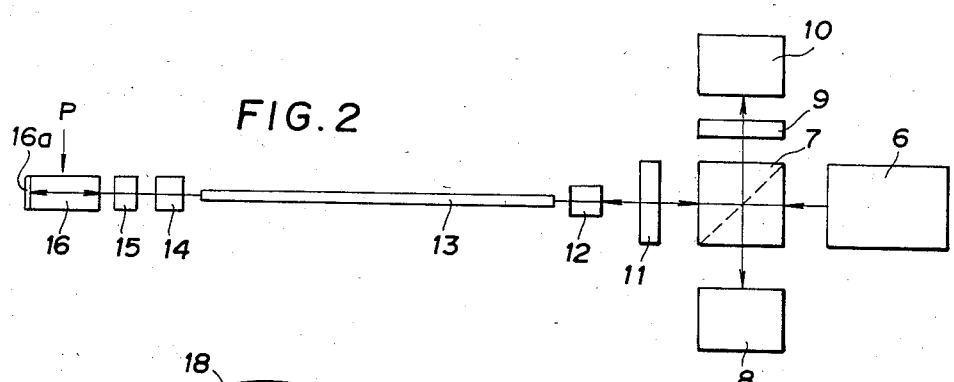
FIG. 2 is a schematic view showing a construction of the catheter-tip micromanometer according to the present invention.
Figure 3:
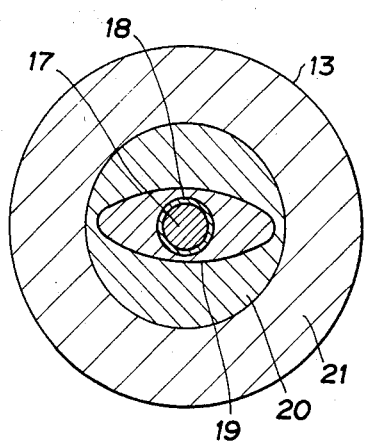
FIG. 3 is an explanatory view, in section, showing an example of a single polarization optical fiber used in the present invention.
Figure 4:
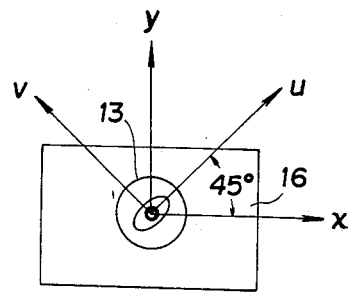
FIG. 4 is an diagramatic view showing a state wherein a single polarization optical fiber used in the present invention is inclined with respect to a photoelastic element at an angle of 45°.

Referring now to the drawings wherein like reference numerals are used throughout the various views to designate like parts and, more particularly, to FIG. 2, according to the present invention, a catheter-tip micromanometer utilizing a single polarization fiber comprises a light source 6 (for example, laser oscillator) for generating coherent light, a beam splitter 7 dividing the light emitted from the light source 6 into two directions, a receptor 8 for monitoring the light source 6, a polarizing plate 9, a receptor 10 for measurement, a ½ wave plate 11, a microlens 12 for focusing light, a single polarization optical fiber 13 for propagating the light from the light source 6, a microlens 14 for focusing light, a ⅛ wave plate 15, and a photoelastic element 16 for causing phase constants of polarized components of light perpendicular to each other due to the pressure to be applied thereto. A means for removing reflected light (for example, isolator) is incorporated in the light source 6 in order that the light source is not adversely affected by the reflected light. The wave plate 11 is an optical element for matching plane of polarization of the light emitted from the light source 6 to either of major axis u and minor axis v of the single polarization fiber 13. As shown in FIG. 3, the single polarization fiber 13 has waveguide function by means of a core 17 and a cladding 18 as single mode optical fiber in accordance with birefringent distortion applied to the core 17 by an elliptical jacket 19 and a support 20 thereby realizing single polarization function. In FIG. 3, reference numeral 21 designates a plastic covering. Intrinsic polarization axis of the single polarization fiber 13 is inclined with respect to direction of stress of the photoelastic element 16 at an angle of 45° (or 135°) as shown in FIG. 4.

Furthermore the photoelastic element 16 is required to possess the following characteristics:

(1) High transmission factor with respect to light
(2) Large photoelastic constant
(3) Safe and stable
(4) Excellent in temperature properties As a relatively suitable material for satisfying the above conditions, there is {111} cut GaP. Epoxy resin has slightly inferior in temperature properties to those of GaP, but high transmission factor as well as large photoelastic constant, so that epoxy resin is comprehensively equivalent to GaP. In addition, $LiNbO_3$, ZnSe, AgBr, AgCl or the like may be utilized. The photoelastic element 16 is provided with a reflector 16a formed by metallizing or the like as shown in FIG. 2.

In operation of the above construction, light beam emitted from the light source 6 is divided by the beam splitter 7 into two directions, and one of the divided light beams is incident into the receptor 8 for monitoring the light source and the other of the divided light beams is incident into the single polarization fiber 13 through the wave plate 11 and the microlens 12. Thus, the light beam linearly polarized is transmitted through the single polarization fiber 13 to the photoelastic element 16 via the microlens 14 and the wave plate 15, and then the light beam is reflected by the reflector 16a, thereafter the reflected light is transmitted through the identical course to that of the incident light in the reverse direction to the wave plate 11. The reflected light is then divided by the beam splitter 7 into two directions. One of the divided reflected light beams proceeds to the side of the light source 6 and the reflected light is absorbed thereby, while the other of the divided reflected light beams is incident into the measuring receptor 10 through the polarizing plate 9.

Such principle that light-receiving level of the receptor 10 changes in response to pressure P applied to the photoelastic element 16 is as follows. First, the case where no wave plate 15 is present will be described.

Polarized light having plane of polarization coinciding with either the major axis u or the minor axis v of the single polarization fiber 13 is incident into the photoelastic element 16. The photoelastic element 16 has x and y axes which exhibit optically different properties, and the x and y axes are inclined with respect to the u and v axes at an angle of 45° as shown in FIG. 4. When pressure P is applied to the photoelastic element 16 in y direction, difference of propagation velocity arises between x polarized component and y polarized component of light. Hence, a phase difference α arises between the x polarized component and y polarized component in the case when light beam is reflected by the reflector 16a and emitted from the photoelastic element 16.

When components u, v, x and y of light are expressed by $e_u, e_v, e_x$ and $e_y$, respectively, the following relationships will be given in plane of incidence into the photoelastic element 16:

$$e_u = a_0 \cos\omega t \quad (1)$$
$$e_v = 0$$

$$e_x = (a_0/\sqrt{2}) \cos\omega t$$

$$e_y = (a_0/\sqrt{2}) \cos\omega t$$

($a_0$: constant, $t$: time)

On the other hand, the following relationships will be given in plane of emittance from the photoelastic element 16:

$$e_x = (a_1/\sqrt{2}) \cos(\omega t + \phi_1) \quad (2)$$

$$e_y = (a_1/\sqrt{2}) \cos(\omega t + \phi_1 + \alpha)$$

$$e_u = (a_1/\sqrt{2}) \sqrt{1 + \cos\alpha} \cos(\omega t + \phi'_1)$$

-continued $$e_v = (a_1/\sqrt{2})\sqrt{1 + \cos\alpha}\, \cos(\omega t + \phi''_1)$$

(wherein $a_1$, $\phi_1$, $\phi'_1$, and $\phi''_1$ are constants)

In these circumstances, phase difference $\alpha$ changes due to pressure P so that levels of u polarized component and v polarized component in reflected light vary also in response thereto. The polarized component u of light propagates independently of the v polarized component in the single polarization fiber 13. Thus, when it is adjusted by the polarizing plate 9 in such that only the light corresponding to the u or v polarized component is received by the receptor 10, light-receiving level change in accordance with $\alpha$ in the same form of function as that of $e_u$ or $e_v$ in equation (2). In general, output voltage E of the receptor 10 is proportional to light power ($e^2u$ or $e^2v$) so that the following equations are given:

$$E = E_1(1 + \cos\alpha),$$

or $$E = E_1(1 - \cos\alpha)\quad (E_1: \text{constant}) \tag{3}$$

Thus it is possible to measure the pressure P as described above.

However, the above expressions may be improper without any modification because expression $\cos\alpha \simeq 1 - \alpha^2$ is valid in case of $P \simeq 0$ ($\alpha << 1$) so that the output voltage E does not substantially change even if the pressure P varies, and sensitivity reduces. In addition to the above, it is also improper that the value E becomes identical in respect of positive and negative pressures (positive and negative $\alpha$), i.e., there is no distinction between the positive and negative pressure. In this connection, the wave plate 15 is applied in the case where pressure of approximatly zero, where positive or negative pressure is measured. When optic axis is adjusted in such that there is a phase difference between x polarized component and y polarized component by wavelength, i.e., $\pi/4$ in the wave plate 15, light reciprocates between the ⅛ wave plate 15 and the reflector 16a in case of pressure P=0, so that there is a phase difference by $(\pi/4) \times 2 = (\pi/2)$ and it turns to circular polarization. Hence when phase difference $\alpha$ is further added due to pressure P, the following relationships will be given as in the aforesaid equations (2):

$$e_x = (a_2/\sqrt{2})\cos(\omega t + \phi_2) \tag{4}$$

$$e_y = (a_2/\sqrt{2})\sin(\omega t + \phi_2 + \alpha)$$

$$e_u = (a_2/\sqrt{2})\sqrt{1 + \sin\alpha}\, \sin(\omega t + \phi'_2)$$

$$e_v = (a_2/\sqrt{2})\sqrt{1 + \sin\alpha}\, \cos(\omega t + \phi''_2)$$

(wherein $a_2$, $\phi_2$, $\phi'_2$, and $\phi''_2$ are constants)

As a result, output E of the receptor 10 at the time when a component corresponding to $e_v$ or $e_u$ is received is expressed as follows:

$$E = E_2(1 + \sin\alpha)$$

or $$E = E_2(1 - \sin\alpha)\quad (E_2: \text{constant}) \tag{5}$$

In accordance with equation (5), changes in the vicinity of as well as changes in positive and negative directions can be measured.

In place of the polarizing plate 9, a polarizing beam splitter 20' may be used as shown in FIG. 10, and outputs $E_u$ and $E_v$ corresponding to two components of light are obtained by means of the receptor 10 and a receptor 21', so that output proportional to $$(E_u - E_v)/(E_u + E_v) \simeq \sin\alpha$$

can be obtained by operation processing, for instance, in a microcomputer.

Figure 6A:
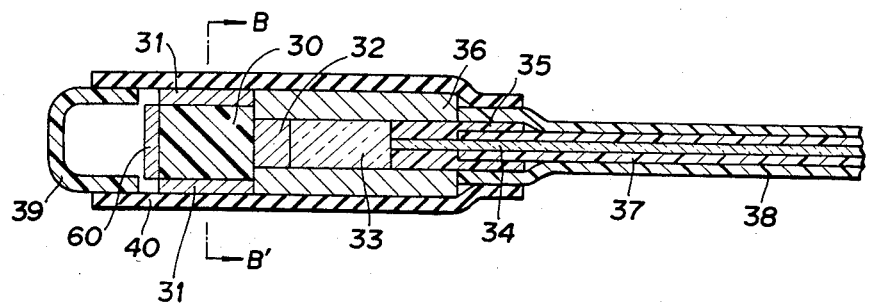
FIG. 6a is a cross-sectional view of a principal part of the catheter-tip micromanometer utilizing a single polarization optical fiber in accordance with an embodiment of the present invention.
Figure 6B:
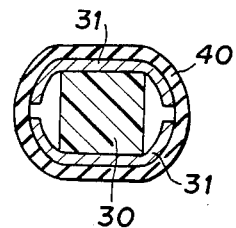

An embodiment of the principal part of the catheter-tip micromanometer according to the present invention will be described hereinbelow by referring to FIGS. 6a and 6b. In FIG. 6a, a photoelastic element 30 is held between metallic plates 31. The photoelastic element 30 is connected to a single polarization fiber 34 through a $\lambda/8$ plate 32 and a rod lens 33. A ceramic or metallic ferrule supports an end portion of the single polarization fiber 34, and a metallic sleeve 36, respectively. The single polarization fiber 34 is covered with a sheath 37, and the sheath is covered with a catheter tube 38. Protector 39 is provided on the extreme end portion of the micromanometer, a rubber waterproof film 40 extends from the protector 39 to the catheter tube 38, and a reflector 60 is also provided. As apparent from FIG. 6b, a photoelastic element 30 is held between metallic plates 31 and it results in the pressure outside a waterproof film 40 being applied only unidirectionally to a photoelastic element 30 (in this case, such pressure is applied from upper side to lower side in FIG. 6b).

Figure 7A:
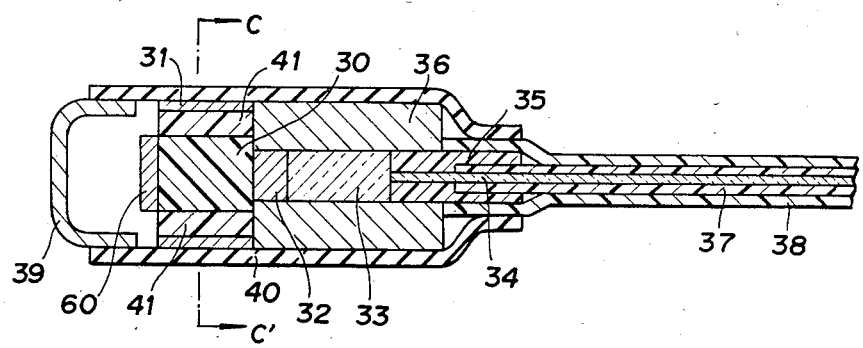
FIG. 7a is a cross-sectional view of a principal part of the catheter-tip micromanometer utilizing a single polarization fiber in accordance with another embodiment of the present invention.
Figure 7B:
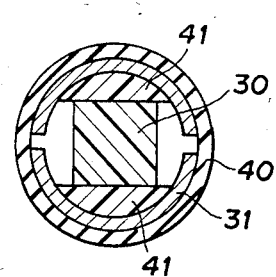

As shown in FIGS. 7a and 7b, the micromanometer according to the present invention includes two spacers 41 for compensating the shape of a photoelastic element 30 interposed between the photoelastic element 30 and one of metalic plates 31 the circumference of which is covered with a waterproof film 40.

Figure 8A:
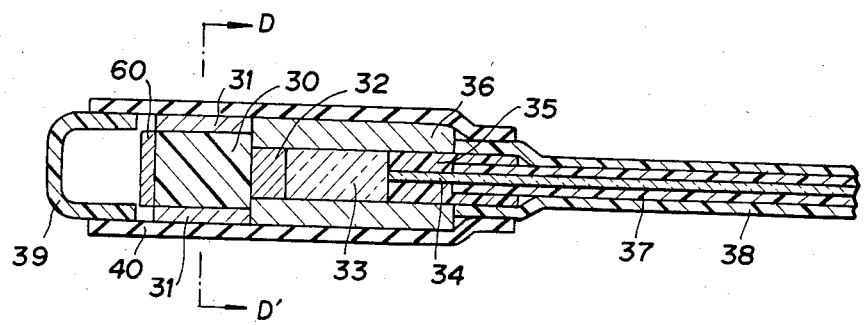
FIG. 8a is a cross-sectional view of a principal part of the catheter-tip micromanometer utilizing a single polarization fiber in accordance with still another embodiment of the present invention.
Figure 8B:
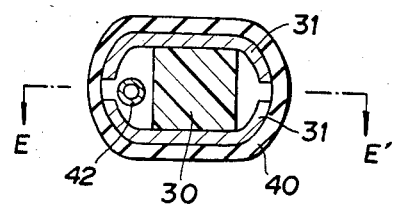
Figure 8C:
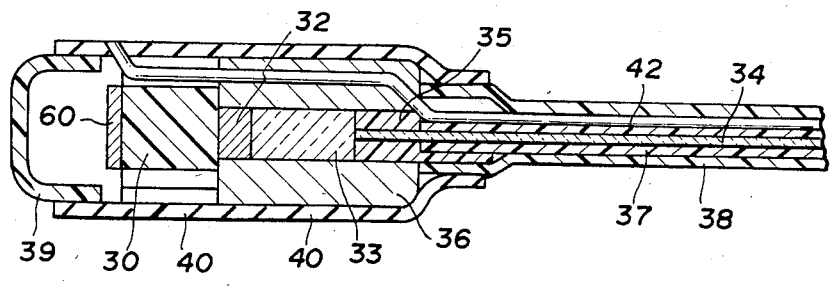
FIG. 8c is a sectional view taken along line E—E' of FIG. 8b.

In the embodiment of FIGS. 8a, 8b and 8c, the micromanometer according to the invention includes a blood-collecting tube 42 held in a space outside the photoelastic element 30 and inside the metallic plates 31, and the circumference of them is covered with the water-proof film 40.

In FIGS. 9a to 9b, a micromanometer comprises a circular metallic member 30 which has a flat mid-partition 31a and a slit portion 31b of the upper side thereof, a plurality of photoelastic elements 31, 49 and 50 positioned in a predetermined distance on the flat mid-partition 31a, a plurality of single polarization fibers 34, 43 and 44 which are respectively connected through rod lenses 33, 45 and 46 and $\lambda/8$ plates 32, 47 and 48 to the photoelastic elements 30, 49 and 50, and a waterproof film 40 to complete a prescribed construction of a micromanometer. The photoelastic elements 30, 49 and 50 are provided, at the reflecting ends, thereof with reflectors 60 while the waterproof film 40 is sealed at its terminal end by a protector 39.

According to the type of the micromanometer illustrated in FIGS. 9a to 9d, blood pressure is measured at plural positions in a human body due to the provision of the plural photoelastic elements 30, 49 and 50. In accordance with the plural data of blood pressure, the deterioration of a vein is easily detected.

In this embodiment, a circular metallic member 31 may be of another material in place of metal, for instance, of rigid plastic or the like.

As described above, since the catheter-tip micromanometer utilizing a single polarization fiber according to the present invention has a construction in which one single polarization fiber and a photoelastic element are used, and light is transmitted through the single polarization fiber as linearly polarized light and incident into the photoelastic element, thereafter the light is reflected by a reflecting means, and the reflected light is then returned through the same course as that of the incident light in the reverse direction (not using any conventional optical fiber bundle and diaphragm), the present catheter-tip micromanometer can be miniaturized and reduced in diameter while maintaining high sensitive performance thereof, besides the present micromanometer can easily be fabricated.

Figure 5:
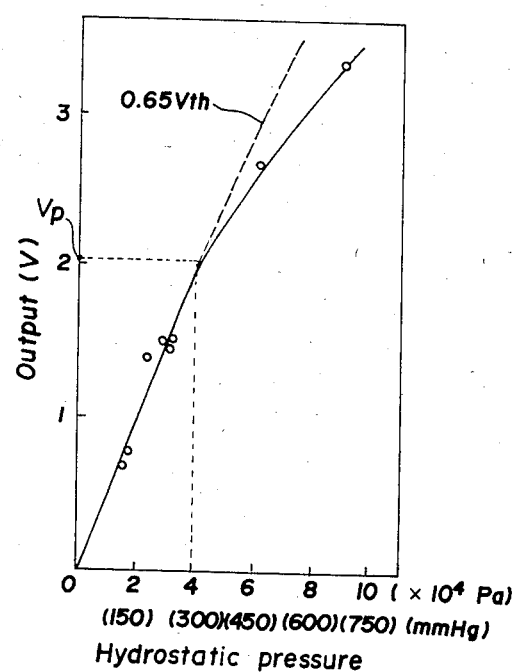
FIG. 5 is a graphical representation indicating a relationship between hydrostatic pressure and output voltage in an embodiment of the present invention.

In the experimental results in FIG. 5 a relationship between an output of a micromanometer according to the present invention and hydrostatic pressure to be applied thereto is plotted. According to the experiment, there was obtained a curve of a solid line which exhibits linearity up to approximately 300 mm Hg ($4 \times 10^4$ pascal). In accordance with this linearity, there was drawn a dotted line the output value of which is of 65% with respect to the theoretical value (Vth). According to the dotted line, sensitivity of 7.0 mV/mm is obtained because 2.1 V (indicated by "Vp") is output when hydrostatic pressure of 300 mm Hg is applied to the micromanometer.

In this experiment, the reason why the output value is reduced by 65% is that the photoelastic element is hardened at both sides thereof by adhesive so that the elasticity of the photoelastic element is reduced.

According to this experiment, further, hydrostatic pressure of 0.73 mm Hg can be detected at the minimum in spite of temperature fluctuation and deterioration with the passage of time.

While the outer diameter of the micromanometer used in the above experiment is 4 mm, it is possible to adopt a photoelastic element with a cross sectional area 1 mm$^2$ or less so that it is easily possible to reduce an outer diameter of a waterproof film on which pressure-receiving surface is positioned approximately up to 1.5 mm.

Furthermore another advantage of the present invention resides in that sensitivity of the micromanometer never does deteriorate in case of miniaturizing and reducing the same in diameter.

Although the present invention has been described with reference to preferred embodiments thereof, many modifications and alterations may be made within the spirit and scope of the present invention.

We claim:

1. A catheter-tip micromanometer utilizing a single polarization optical fiber, the micromanometer comprising:
   a photoelastic element, the light, propagation constants of which change in two axes perpendicular to each other along a propagating direction in accordance with blood pressure to be applied thereto;
   a single polarization optical fiber, one end of which faces an incidence point of said photoelastic element, said fiber having a linearly polarized axis which is positioned at a prescribed angle with respect to one of said two axes of said photoelastic element;
   a light reflecting means positioned at an opposite side of said photoelastic element facing said one end of the single polarization optical fiber;
   a light source means positioned to face the other end of said single polarization optical fiber for emitting light which propagates along said linearly polarized axis of said single polarization optical fiber and reaches said incidence point of said photoelastic element; and
   a detection means for detecting blood pressure to be applied to said photoelastic element based on the light emitted from said light source means and the reflected light reflected by said reflecting means and from the other end of said single polarization optical fiber back through said photoelastic element and to said single polarization optical fiber.

2. A catheter-tip micromanometer as claimed in claim 1 wherein said photoelastic element is composed of a material selected from the group consisting of {111} cut GaP, epoxy resin, LiNbO$_3$, ZnSe, AgBr and AgCl.

3. A catheter-tip micromanometer as claimed in claim 1 wherein said light reflecting means is composed of a reflector fixed to an end of said photoelastic element which is opposite to said incidence point thereof by means of metallizing or the like.

4. A catheter-tip micromanometer as claimed in claim 1 wherein said single polarization optical fiber is composed of a core, a cladding positioned about said core, an elliptical jacket positioned about said cladding, and a support positioned about said elliptical jacket.

5. A catheter-tip micromanometer as claimed in claim 1 wherein said prescribed angle is 45° or 135°.

6. A catheter-tip micromanometer as claimed in claim 1 wherein there are provided a plurality of photoelastic elements disposed at plural points where blood pressure is to be measured, and a plurality of single polarization optical fibers connected respectively to said plural photoelastic elements.

7. A catheter-tip micromanometer as claimed in claim 1 wherein said photoelastic element is held between a couple of protective plates such that blood pressure is applied to said photoelastic element in only a single axial direction of two axes perpendicular to each other and no blood pressure is applied in the other axial direction.

8. A catheter-tip micromanometer as claimed in claim 1 wherein a ⅛ wave plate is disposed between said photoelastic element and said single polarization optical fiber.

9. A catheter-tip micromanometer as claimed in claim 1 wherein a ½ wave plate is disposed between said single polarization optical fiber and said detection means.

10. A catheter-tip micromanometer as claimed in claim 1 wherein said light source means is provided with a means for removing reflected light coming back to said light source means.

11. A catheter-tip micromanometer as claimed in claim 1 wherein a blood-collecting tube having a blood-collecting opening communication to the outside of said micromanometer is placed in said micromanometer.

* * * * *